United States Patent [19]

Hartman et al.

[11] Patent Number: 4,506,094
[45] Date of Patent: Mar. 19, 1985

[54] CYCLOALKYLSULFONATES, POLYMERS AND PROCESSES RELATING TO SAME

[75] Inventors: Susan E. Hartman; Michael E. Allen; William E. Pascoe, all of Rochester, N.Y.

[73] Assignee: Eastman Kodak Company, Rochester, N.Y.

[21] Appl. No.: 471,385

[22] Filed: Mar. 2, 1983

Related U.S. Application Data

[62] Division of Ser. No. 324,238, Nov. 23, 1981, Pat. No. 4,433,130.

[51] Int. Cl.³ .................................... C07C 143/20
[52] U.S. Cl. .............................. 560/118; 430/271; 430/285; 430/941
[58] Field of Search ........................................ 560/118

[56] References Cited

U.S. PATENT DOCUMENTS

| | | | |
|---|---|---|---|
| T926,013 | 9/1974 | Thompson | 528/308 |
| 3,853,820 | 12/1974 | Vachon | 528/302 |
| 3,929,489 | 12/1975 | Arcesi et al. | 430/300 |
| 4,167,395 | 9/1979 | Engelhardt et al. | 8/557 |
| 4,374,194 | 2/1983 | McGuckin et al. | 430/271 |

FOREIGN PATENT DOCUMENTS

| | | | |
|---|---|---|---|
| 0081925 | 6/1983 | European Pat. Off. | 560/118 |
| 1470059 | 4/1977 | United Kingdom . | |

OTHER PUBLICATIONS

*Research Disclosure*, vol. 204, pp. 167–172, (1981).

Primary Examiner—Natalie Trousof
Assistant Examiner—Patricia M. Scott
Attorney, Agent, or Firm—Arthur H. Rosenstein

[57] ABSTRACT

A novel compound having the formula:

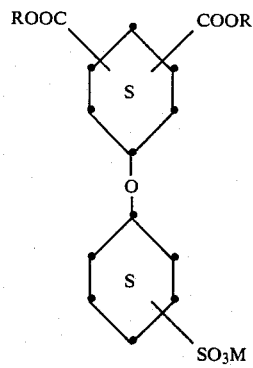

wherein:
R is alkyl containing from 1 to 10 carbon atoms; and
M is a monovalent cation, selected from the group consisting of alkali metal and ammonium, has been synthesized in high yield by hydrogenating the corresponding arylsulfonate in a solvent which simultaneously prevents hydration of the sulfonate group and hydrolysis of the ester functions. The compound is useful in preparing condensation polymers having ionic groups. In particular, these condensation polymers comprise additional polymerized copolymerizable dicarboxylic acids and diols, diamines or hydroxyamines, to yield polyesterionomers useful in dye imbibition photohardenable imaging materials for forming positive dye images.

6 Claims, No Drawings

CYCLOALKYLSULFONATES, POLYMERS AND PROCESSES RELATING TO SAME

This is a division of application Ser. No. 324,238, filed Nov. 23, 1981, now U.S. Pat. No. 4,433,130.

BACKGROUND OF THE INVENTION

1. Field of the Invention

This invention relates to novel cycloalkylsulfonates which are useful in preparing polymers. The polymers are particularly useful in the photographic arts. In one of its aspects, this invention relates to the use of the compounds to prepare polymers which are incorporated into radiation-sensitive elements. In another of its aspects, this invention relates to the preparation of such compounds.

2. Description Relative to the Prior Art

The polymerization of aromatic sulfonates with other dicarboxylic acids and diols to form ionic polyesters is known in the art. For instance, U.S. Pat. No. 4,167,395 issued Sept. 11, 1979, discloses a water-soluble polyester containing recurring units derived from dimethyl 5-(p-sodiosulfophenoxy)isophthalate. However, when polyesters containing this solubilizing aromatic sulfonate compound are brought into contact with ordinary tap water, they exhibit scumming due to an exchange of sodium ions with the mono-, di- and trivalent ions in tap water. Therefore, the use of these aromatic sulfonate polyesters which requires contact with water, also requires the use of carefully distilled or deionized water and an environment free from the exchanging anions causing the undesirable scumming.

Problems have also been encountered with alkyl sulfonates, which are generally thermally unstable at the temperatures needed to prepare polyesters by standard melt polymerization techniques.

U.S. Pat. No. 3,682,866, issued Aug. 8, 1972, discloses that cyclohexanesulfonates, such as sodium 1,3-dicarboxycyclohexane-5-sulfonic acid, is prepared by hydrogenating an aqueous solution of the corresponding aromatic sulfonate in the presence of a palladized carbon catalyst. However, attempts to prepare the dimethyl ester of this cycloalkyl compound in accordance with the disclosed procedure have not resulted in successfully polymerizable compounds. During the aqueous hydrogenation procedure the ester function is hydrolyzed to a great extent to the free diacid, as well as other compounds, which composition is polymerizable only with great difficulty due to its high melting point. The "polymers" obtained from these compounds are very low in viscosity and are contaminated with considerable amounts of unpolymerized free acid. Thus, they are useless for most purposes for which ionic polyesters are sought. Further, the attempted condensation polymerization of these diacids releases water which is extremely difficult to remove completely from a polymer melt. Volatile alcohols which are easily removed are given off during the condensation of a lower alkyl diester.

It is surprising that 1,3-dicarboxycyclohexane-5-sulfonate esters, even if obtainable in unhydrolyzed, easily polymerizable form, improve the solubility of a polyester to a significantly greater degree than the use of aromatic sulfonate compounds. The sulfonate group of a 1,3-dicarboxycyclohexane-5-sulfonate is relatively close to the carbon backbone, and the resulting steric hindrance is expected to reduce the effectiveness of the sulfonate moiety as a solubilizing group.

It would be highly desirable to obtain cycloalkylsulfonates in unhydrolyzed, easily polymerizable form, which are thermally stable at temperatures required by standard melt polymerization techniques. A method of making these compounds in good yield is also desirable. Still further, it would be desirable to obtain condensation polymers which would not tend to exchange ions with other cations in surrounding aqueous environments. Such condensation polymers exhibiting improved salt tolerance would be useful in the presence of ordinary tap water, rather than requiring the use of expensive distilled or deionized water to avoid scumming and insolubilization of the polymer.

SUMMARY OF THE INVENTION

The present invention provides cycloalkylsulfonates having the formula:

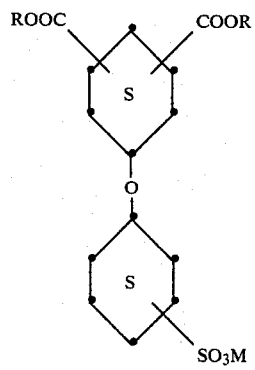

wherein:

R is alkyl containing from 1 to 10 carbon atoms; and

M is an alkali metal or ammonium cation, which are readily polymerizable and thermally stable at temperatures required by standard melt polymerization techniques. The present invention also provides condensation polymers comprising:

(a) from 0.1 to 70 mole percent of recurring units of the above-described compound;

(b) 30 to 99.9 mole percent of one or more additional polymerized copolymerizable polycarboxylic acids; and (c) the requisite stoichiometric quantities (100 mole percent total) of at least one polymerized copolymerizable polyfunctional diol, diamine or hydroxyamine.

It is noted that all mole percentages are based on the conventional polyester designations wherein the acids are described in terms of the acid component of the polyester and the diol, diamine or hydroxyamine percentages are disclosed in terms of the corresponding base component of the polyester.

The condensation polymers of the present invention are useful in many applications, but are particularly useful as copolymers in dye imbibition photohardenable imaging materials which have positive color proofing applications and are water-developable, as described in copending U.S. application Ser. No. 214,144, filed Dec. 8, 1980 by McGuckin, Hartman and Specht, now abandoned. Copolymers containing the condensed compounds of the invention exhibit improved salt tolerance and therefore are completely developable in ordinary tap water.

The condensation polymers of the invention are also useful in aqueous processable negative-working lithographic plates and photoresist materials, including lithoplates designed for laser exposure; liquid toner formulations and water-based heat transfer printing inks; dyeable fabrics and fiber-forming condensation polymers; hair setting lotions; textile sizes; water-soluble or hot-melt adhesives and additives for adhesives; and coating and packaging materials.

In another aspect of the present invention, a process of preparing the above-described compounds, in high yield, comprises the steps of:

(a) dissolving an aromatic compound having the formula:

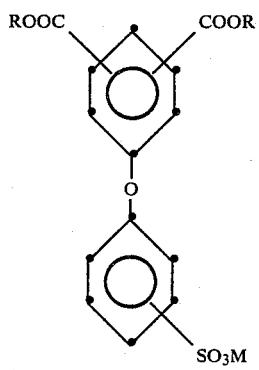

wherein:

R and M are as defined above, said aromatic compound being substantially free of hydrated species, in a solvent which substantially prevents hydration of the sulfonate group of said formula and simultaneously prevents hydrolysis of the ester functions of said formula during hydrogenation;

(b) hydrogenating the solution of step (a) in the presence of hydrogenation catalyst; and (c) isolating the compound of the present invention.

In still another aspect of the present invention, a process of preparing polymers from the above-described compound comprises preparing the compound as previously described and polymerizing the compound isolated in step (c) with (i) from 30 to 99.9 mole percent of one or more additional copolymerizable polycarboxylic acids or esters, anhydrides or acid halides thereof; and (ii) the requisite stoichiometric quantities (100 mole percent total) of each of at least one polymerizable polyfunctional diol, diamine or hydroxyamine.

DETAILED DESCRIPTION OF PREFERRED EMBODIMENTS

The novel composition of matter is represented by the formula:

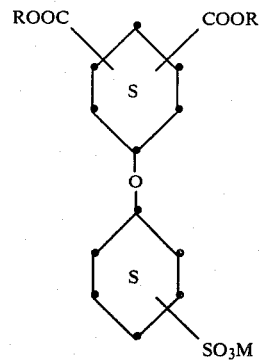

wherein:

R is alkyl containing from 1 to 10 carbon atoms, such as methyl, ethyl, propyl, isopropyl, n-butyl, secondary butyl, isobutyl, t-butyl, pentyl, neopentyl, hexyl, octyl or decyl; and M is a monovalent cation selected from the group consisting of an alkali metal cation as exemplified by lithium, sodium, potassium or rubidium; and ammonium including quaternary ammonium salts.

The —COOR groups occupy any ring position except that occupied by the oxygen which links the two cyclohexylene rings, but preferably occupy positions which are meta with respect to each other, and most preferably meta with respect to the position occupied by the oxygen linking group as well.

The —$SO_3M$ group also occupies any ring position except that occupied by the oxygen linking the two cyclohexylene rings, but preferably occupies a position which is para with respect to the oxygen linking group.

Examples of compounds useful herein include:
dimethyl 5-(4-sodiosulfocyclohexyloxy)-1,3-cyclohexanedicarboxylate,
dimethyl 3-(4-sodiosulfocyclohexyloxy)-1,2-cyclohexanedicarboxylate,
dimethyl 4-(4-sodiosulfocyclohexyloxy)-1,2-cyclohexanedicaboxylate,
dimethyl 4-(4-sodiosulfocyclohexyloxy)-1,3-cyclohexanedicarboxylate,
dimethyl 5-(4-sodiosulfocyclohexyloxy)-1,2-cyclohexanedicarboxylate,
dimethyl 3-(4-sodiosulfocyclohexyloxy)-1,4-cyclohexanedicarboxylate,
dimethyl 6-(4-sodiosulfocyclohexyloxy)-1,3-cyclohexanedicarboxylate,
diethyl 5-(4-sodiosulfocyclohexyloxy)-1,3-cyclohexanedicarboxylate,
diisopropyl 5-(4-sodiosulfocyclohexyloxy)-1,3-cyclohexanedicarboxylate,
dimethyl 5-(4-potassiosulfocyclohexyloxy)-1,3-cyclohexanedicarboxylate,
dimethyl 5-(2-sodiosulfocyclohexyloxy)-1,3-cyclohexanedicarboxylate, and
dimethyl 5-(3-sodiosulfocyclohexyloxy)-1,3-cyclohexanedicarboxylate.

The preferred compound has the formula:

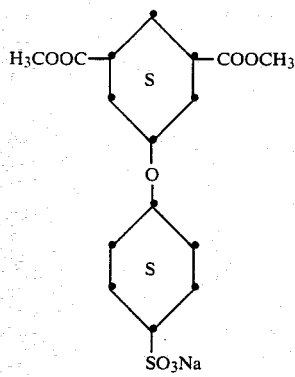

The process of preparing the compounds of the present invention comprises the steps of:

(a) dissolving an aromatic compound having the formula:

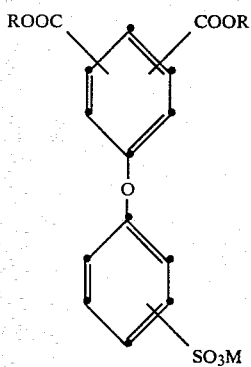

wherein R and M are as defined above, said aromatic compound being substantially free of hydrated species, in a solvent which substantially prevents hydration of the sulfonate group of said formula and simultaneously substantially prevents hydrolysis of the ester functions of said formula during hydrogenation;

(b) hydrogenating the solution of step (a) in the presence of a hydrogenation catalyst; and (c) isolating the compound of the present invention.

Examples of aromatic compounds useful herein include:
dimethyl 5-(4-sodiosulfophenoxy)isophthalate;
dimethyl 3-(4-sodiosulfophenoxy)phthalate;
dimethyl 4-(4-sodiosulfophenoxy)phthalate;
dimethyl 4-(4-sodiosulfophenoxy)isophthalate;
dimethyl 5-(4-sodiosulfophenoxy)phthalate;
dimethyl 3-(4-sodiosulfophenoxy)terephthalate;
dimethyl 6-(4-sodiosulfophenoxy)isophthalate;
diethyl 5-(4-sodiosulfophenoxy)isophthalate;
diisopropyl 5-(4-sodiosulfophenoxy)isophthalate;
dimethyl 5-(4-potassiosulfophenoxy)isophthalate;
dimethyl 5-(2-sodiosulfophenoxy)isophthalate; and
dimethyl 5-(3-sodiosulfophenoxy)isophthalate.

It is critical to the present invention that the aromatic compound of step (a) be substantially free of hydrated species. When the sulfonate group of the aromatic compound is hydrated to any appreciable degree, the yield of unhydrated compound is decreased. More importantly, a substantial amount of hydrated compound is produced which exhibits a melting point too high (generally greater than 300° C.) to allow melting and polymerization at standard melt polymerization temperatures (about 200° to 280° C.). Further, once a substantial amount of the hydrate of the aromatic compound is present in solution, more hydration of the sulfonate group tends to occur during the hydrogenation reaction itself, resulting in the formation of essentially non-polymerizable material.

The aromatic compound substantially free of hydrated species is obtainable by recrystallization from an appropriate solvent such as an aqueous alcohol. However, the selection of the solvent composition is variable for different batches of aromatic material, necessitating the use of just enough water to selectively dissolve the desired material but not so much water that further hydration of the sulfonate group occurs. It is noted that a highly dilute solution may not require the addition of water.

The preferred method for obtaining the aromatic compound substantially free of hydrated species is to heat a mixture of the aromatic compound including any hydrates of the aromatic compound at a temperature of at least 175° C. until substantially all hydrates have been converted to the aromatic compound in its unhydrated state. The time required to convert all hydrates of the aromatic compound to the aromatic compound in its unhydrated state varies from about 5 to about 48 hours, but generally is about 24 hours.

The solvent in which the organic compound substantially free of hydrated species is dissolved is any solvent which substantially prevents hydration of the sulfonate group of the aromatic compound and, simultaneously, substantially prevents hydrolysis of the ester functions of the aromatic compound. Preferably, the solvent comprises: (i) from about 70 to about 80 percent by volume of an alcohol having the formula $R^1OH$ wherein $R^1$ is alkyl having from 1 to 10 carbon atoms; (ii) from about 20 to about 23 percent by volume of water; and (iii) from about 2 to about 5 percent by volume of an acid preferably having a dissociation constant of not more than $2.0 \times 10^{-5}$ at 25° C. The solvent should contain only enough water to completely dissolve the aromatic compound, and enough of the alcohol and the acid to substantially prevent hydration or hydrolysis of the aromatic compound during the hydrogenation reaction.

Examples of the alcohol component of the solvent include methanol, ethanol, isopropanol, n-butanol, secondary butanol, isobutanol, t-butanol, pentanol, neopentanol, hexanol, octanol and decanol. The alcohol is preferably selected by matching the alkyl group of the alcohol to the alkyl group in the ester functions of the aromatic compound. This advantageously prevents ester exchange of the alkyl groups during the hydrogenation reaction. Most preferably the alcohol is methanol.

The acid of the solvent is any acid, preferably a weak acid having a dissociation constant of not more than $2.0 \times 10^{-5}$ at 25° C., such as acetic acid, arsenious acid, boric acid and 1-butanoic acid. The preferred acid is acetic acid.

Examples of the preferred solvent include methanol, water and acetic acid (75:23:2 by volume); methanol, water and acetic acid (75:20:5 by volume); and methanol, water and 0.1 to 0.2 percent HCl or $H_2SO_4$ or 4 to 5 percent p-toluenesulfonic acid. The most preferred solvent is methanol, water and acetic acid (75:23:2 by volume).

The amount of solvent is not critical but preferably varies from about 75 to about 99 weight percent of the solution.

The solution of the aromatic compound is hydrogenated in the presence of a hydrogenation catalyst. The hydrogenation catalyst employed is any hydrogenation catalyst which is strong enough to cause hydrogenation of the benzene rings of the aromatic compound. Examples of effective hydrogenation catalysts include rhodium over carbon, ruthenium over carbon, palladium over carbon and platinum over carbon. Rhodium over carbon is preferred.

The hydrogenation reaction is carried out under a pressure of about 500 to about 5000 psi, preferably at about 2500 psi. The hydrogenation reaction generally proceeds at a temperature between about 30° and about 175° C., and preferably between about 100° and 130° C.

The reaction time is a function of reaction temperature, pressure, the solvent selected, the hydrogenation catalyst selected and the particular aromatic compound employed. In general, reaction times are between about 4 and about 24 hours, with shorter times being employed with more active solvents and catalysts and longer times for less active solvents and catalysts.

The compound of the present invention is isolated by
(i) removing the effective hydrogenation catalyst, for example, by filtration, decantation, centrifugation followed by decantation or other methods known in the art;
(ii) removing the solvent employed during the hydrogenation reaction, for example, by evaporation; and
(iii) removing any hydrates of the compound formed during the hydrogenation reaction.

The hydrates of the compound are preferably removed by mixing the product of step (ii) with a solvent such as acetone, filtering off the insoluble hydrates and evaporating the solvent from the remaining filtrate containing the compound of the present invention in its unhydrated state.

The cycloalkylsulfonates are obtained as the readily polymerizable diester, substantially free of high melting hydrated species, and are useful in preparing the condensation polymers of the present invention.

The condensation polymer of the invention is one comprising:
(a) from 0.1 to 70 mole percent of recurring units having the formula:

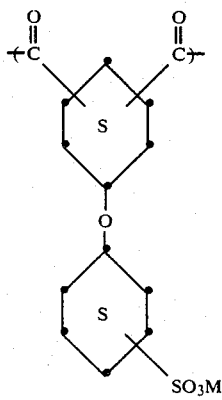

wherein M is a monovalent cation selected from the group consisting of alkali metal and ammonium;

(b) 30 to 99.9 mole percent of one or more additional polymerized copolymerizable polycarboxylic acids; and
(c) 100 mole percent total of at least one polymerized polyfunctional diol, diamine or hydroxyamine. A particularly preferred condensation polymer is one comprising from about 20 to about 40 mole percent of the recurring unit of (a) above.

Examples of recurring units derived from additional polymerized copolymerizable polycarboxylic acids useful herein include those having the formula:

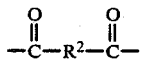

wherein $R^2$ is an arylene group such as phenylene and naphthalene; a straight or branched chain alkylene such as ethylene, propylene, butylene, 2,2-dimethyl-1,3-propylene, 2-ethyl-2-methyl-1,3-propylene or 1,10-decylene; a polycyclylene or arylenebisalkylene; a group such as those having the following structures:

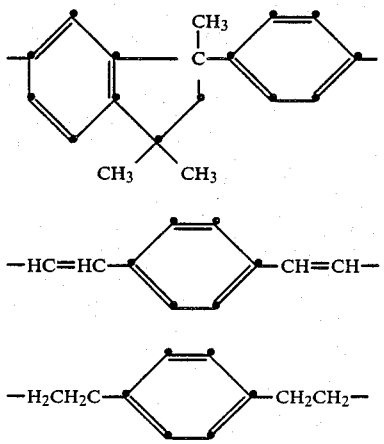

and corresponding derivatives, such as dianhydrides, diacid chlorides and di(lower alkyl) esters, preferably having from 1 to 6 carbon atoms, such as methyl, ethyl, propyl, isopropyl or butyl. It is noted that throughout the specification and claims the terms "alkylene" and "arylene" include substituted alkylene and arylene such as chloroethylene, phenoxyphenylene, carboxyphenylene, bromonaphthylene and 3-phenyl-1,1,3-trimethyl-5,4'-indanylene.

Preferred additional copolymerizable polycarboxylic acids comprise a mixture of such acids which provide recurring units having the formulae:

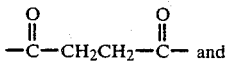 and

Examples of recurring units derived from polymerized polyfunctional diols, diamines or hydroxyamines include units from diols such as those having the formula

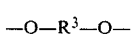

wherein R³ is straight or branched chain alkylene such as ethylene, propylene, butylene, trimethylene, 2,2-dimethyl-1,3-propylene, 2-ethyl-2-methyl-1,3-propylene and 1,10-decylene; cycloalkylene such as 1,4-cyclohexylene and 1,4-cyclohexylenedimethylene; aliphatic ether such as oxydiethylene and ethylenebis(oxyethylene); cycloalkylene ether such as

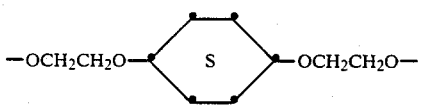

or units derived from bisphenols such as 4,4'-isopropylidenediphenylene.

Copolymerizable diols, diamines and hydroxyamines which are useful in the condensation polymers of the present invention include ethylene glycol, diethylene glycol, 1,3-propanediol, 1,4-butanediol, 1,5-pentanediol, 1,6-hexanediol, 1,7-heptanediol, 1,8-octanediol, neopentyl glycol, 2,2-diethyltrimethylenediol, 1,3-cyclohexanedimethanol, 1,4-cyclohexanedimethanol, triethylene glycol, tetraethylene glycol, 2,3-norbornanediol, 2,5(6)-norbornanediol, 1,4-bis(2-hydroxyethoxy)cyclohexane, 1,4-bis(2-hydroxypropoxy)cyclohexane, 2-ethyl-2-n-butyl-1,3-propanediol, 5-dimethylamino-m-xylene-α,α'-diol, 2-butene-1,4-diol, 1,3-bis(2-hydroxyethyl)-5,5-dimethylhydantoin ethylenediamine, 1,6-hexanediamine, 1,4-cyclohexanebis(methylamine), N,N-dimethylhexamethylenediamine, 4,4'-isopropylidenediphenol, p,p'-biphenol, 4,4'-oxybisphenol, 2,7-naphthalenediol, p-phenylenediamine, 4,4'-diphenylmethanediol, 1,8-naphthalenediol and 4-(aminomethyl)cyclohexanemethanol-2-aminoethanol.

Preferred copolymerizable polyfunctional diols, diamines or hydroxyamines which are especially useful include copolymerizable diols. A particularly preferred copolymerizable diol provides recurring units of the structure:

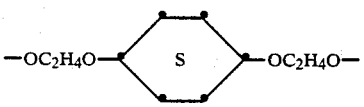

Exemplary condensation polymers of the present invention include poly[1,4-cyclohexylenebis(oxyethylene)succinate-co-p-phenylenebis(acrylate)-co-5-(4-sodiosulfocyclohexyloxy)-1,3-cyclohexanedicarboxylate], poly[1,4-cyclohexylenebis(oxyethylene)terephthalate-co-5-(4-sodiosulfocyclohexyloxy)-1,3-cyclcohexanedicarboxylate], poly[2,2-dimethylpropylene-co-oxydiethylene 3-phenyl-1,1,3-trimethylindan-5,4'-dicarboxylate-co-p-phenylenebis(propionate)-co-5-(4-sodiosulfocyclohexyloxy)-1,3-cyclohexanedicarboxylate], poly[ethylene-co-2,2-dimethylpropylene 3-phenyl-1,1,3-trimethylindan-5,4'-dicarboxylate-co-p-phenylenebis(propionate)-co-5-(4-sodiosulfocyclohexyloxy)-1,3-cyclohexanedicarboxylate], a polyester amide of 40 mole percent 1,4-bis(2-hydroxyethoxy)cyclohexanone, 60 mole percent 1,6-hexanediamine, 20 mole percent succinic acid, 40 mole percent 1,4-phenylenedicarboxylic acid and 40 mole percent of 5-(4-sodiosulfocyclohexyloxy-1,3-cyclohexanedicarboxylic acid and a polyester-amide of 60 mole percent 1,4-bis-(2-hydroxyethoxy)cyclohexane, 40 mole percent 3-aminopropanol, 15 mole percent succinic acid, 55 mole percent 1,4-phenylenediacrylic acid and 30 mole percent 5-(4-sodiosulfoxycyclohexaloxy-1,3-cyclohexanedicarboxylic acid.

The process of preparing the condensation polymers of the present invention comprises two steps, the first being that of making the cycloalkylsulfonates by the method described above. The second step comprises the copolymerization of these compounds with copolymerizable polyfunctional diols, diamines or hydroxyamines with optional additional copolymerizable polycarboxylic acids, anhydrides, esters or acid chlorides.

Condensation polymerization is carried out using techniques well known in the polymer chemistry art, including melt, powder, bulk, suspension and solution techniques. However, the preferred mode of preparing the condensation polymer disclosed herein is by employing standard melt polymerization techniques. The desired polyfunctional diols, diamines and/or hydroxyamines are heated to a melt with the desired polycarboxylic acids or anhydrides, esters or acid chlorides thereof on an approximately equal molar basis or excess of polyfunctional diol, diamine or hydroxyamine. As a practical matter, it is frequently desirable to utilize an excess of up to 100 molar percent of the polyfunctional diols, diamines and/or hydroxyamines in the reaction mixture. The temperature employed generally varies between about 200° and about 280° C. When a homogeneous melt has been achieved, the reaction mixture is treated with a transesterification catalyst such as an alkali or alkaline earth metal carbonate, oxide, hydroxide, hydride or alkoxide, or a compound of the Group IVB metals of the periodic table, such as tetraisopropyl orthotitanate, butyl titanate, organometallic halides, and complex alkoxides such as NaHTi(OC₄H₉)₂. Low-boiling alcohols such as methanol are removed by distillation during the polymerization. The reaction mixture is then optionally placed under reduced atmosphere, generally ranging from about 0.02 to about 50 millimeters with constant stirring until the desired degree of polymerization has been reached (generally between about 10 to about 240 minutes). When the polymerization is complete, the viscous melt is cooled to obtain the resulting condensation polymer.

The inherent viscosities of the condensation polymers of the present invention are subject to wide variation, but generally are within the range from about 0.10 to 4.5 and preferably from about 0.15 to 0.5, as measured (unless otherwise indicated in the specification) in a 1:1 weight mixture of phenol:chlorobenzene at 25° C. at a concentration of 0.25 grams/100 ml of solution. As used herein, the term "inherent viscosity" is determined by the formula:

$$\eta_{inh} = \frac{2.30 \log \eta_{rel}}{C}$$

wherein:

$\eta_{inh}$ is the inherent viscosity;

$\eta_{rel}$ is the relative viscosity of 1:1 phenol:chlorobenzene solution of the polymer; and C is the concentration in grams (0.25) of polymer per 100 cc of solution.

The polymers of the present invention typically have glass transition temperatures within the range of about −10° to about 200° C. These temperatures are determined by differential scanning colorimetry, as disclosed in *Techniques and Methods of Polymer Evaluation*, Volume 2, Marcel Dekker, Inc., New York, 1970.

The condensation polymers of the present invention are useful in a variety of applications which require contact with water or aqueous solutions. For example, the condensation polymers of the present invention are particularly useful in dye imbibition photohardenable imaging materials which are water-developable, as described in copending U.S. application Ser. No. 214,144, now abandoned. When contacted by water containing ions such as $Mg^{++}$ and $Ca^{++}$, the condensation polymers of the invention do not demonstrate undesirable salt sensitivity. That is, they do not exhibit ion exchange and the accompanying undesirable scumming problems associated with polymers containing aromatic sulfonate rather than the cycloalkylsulfonate recurring units of the present invention. These salt-tolerant condensation polymers are developable in ordinary, inexpensive tap water, and do not require the use of more costly distilled or deionized water.

This invention is further illustrated by the following examples.

PREPARATION 1

Preparation of dimethyl 5-(4-sodiosulfophenoxy)isophthalate, substantially free of hydrated species A mixture of dimethyl 5-(4-sodiosulfophenoxy)isophthalate and its hydrates was heated for 24 hours at 200° C. to convert substantially all hydrates to the aromatic compound in its unhydrated state. A nuclear magnetic resonance spectrum of the resulting material in dry DMSO (deuterated dimethyl sulfoxide) appeared approximately as follows:

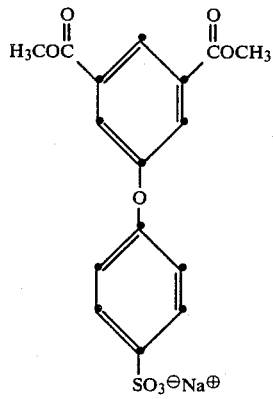

The above spectrum completely lacked the sharp singlet at about δ3.4 present in nuclear magnetic resonance spectra of mixtures of hydrated and unhydrated species of the aromatic compound. The disappearance of this peak indicated complete removal of the water of hydration, leaving dimethyl 5-(4-sodiosulfophenoxy)isophthalate substantially free of hydrated species.

EXAMPLE 1

Preparation of dimethyl 5-(4-sodiosulfocyclohexyloxy)-1,3-cyclohexanedicarboxylate About 200.0 grams of the dimethyl 5-(4-sodiosulfophenoxy)isophthalate prepared in Preparation 1 was dissolved in about 1600 ml of a mixture of methanol, water and acetic acid (75:23:2 by volume). About 30.0 grams of rhodium over carbon catalyst was added. The mixture was shaken under a pressure of 2500 psi at a temperature of 115° C. for 4 hours. After removing the catalyst by filtration, the solvent was evaporated, and the oily residue triturated in dry acetone. A nuclear magnetic resonance spectrum of the acetone-insoluble solid, removed by filtration, indicated the presence of the hydrate of the desired compound, a small quantity of the diacid of the compound and very little residual starting material. The acetone-soluble fraction (filtrate) contained almost exclusively the unhydrated diester. On evaporation of the acetone, about 100 grams of a white solid material were obtained. A nuclear magnetic resonance spectrum of this material was run in dry DMSO and values were assigned to the following protons:

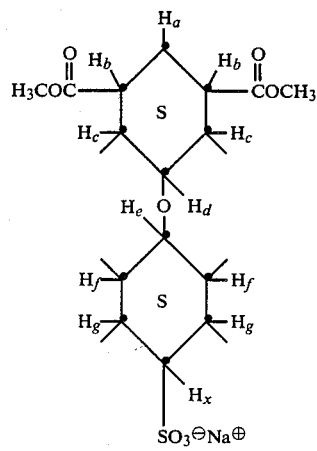

δ0.8 to 2.5 ($H_a$, $H_b$, $H_c$, $H_f$ and $H_g$, very complex section of the spectrum that was not resolved), 3.6 ($CH_3$), about 3.6 ($H_d$ and $H_e$, partially masked by $CH_3$). $H_x$ was a broad multiplet that was not positively located. If the hydrate had been present, a singlet would have been present at 3.3–3.4δ, which would have disappeared when $D_2O$ was added to the sample. No such singlet was present in this spectrum.

The success of hydrogenation was determined by examining the aromatic region (δ7.7 to 8.1) of the NMR spectrum. The aromatic protons of any residual aromatic starting material would have been quite apparent in this region, but were totally lacking, indicating that the hydrogenation reaction was at least 95 percent complete.

EXAMPLE 2

Condensation polymerization of dimethyl 5-(4-sodiosulfocyclohexyloxy)-1,3-cyclohexane dicarboxylate The following reactants, in the amounts specified were weighed into a 50 ml, round-bottomed flask.

| Compound | Percent of Composition | Mole | g |
|---|---|---|---|
| HOC$_2$H$_4$O—⟨S⟩—OC$_2$H$_4$OH | 100% + 20% excess | 0.06 | 12.04 |
| H$_5$C$_2$OC(=O)—C$_2$H$_4$—C(=O)—OC$_2$H$_5$ | 10 | 0.005 | 0.17 |
| H$_5$C$_2$OC(=O)—HC=CH—⟨⟩—CH=CH—C(=O)OC$_2$H$_5$ | 55 | 0.0275 | 7.59 |
| H$_3$COC(=O)—⟨S⟩—C(=O)OCH$_3$ with O-linked ⟨S⟩—SO$_3^⊖$Na$^⊕$ | 35 | 0.0175 | 7.0 |

The flask was flushed with a slow stream of nitrogen for 15 minutes and then immersed into a 215° C. salt bath. While still under a nitrogen atmosphere, the reactants were allowed to come to a clear melt before adding two drops of tetra-isopropyl orthotitanate catalyst. After collecting the theoretical yield of alcohols over about 90 minutes, the reaction mixture was placed under a 0.1 mm atmosphere with constant stirring controlled by a Cole-Parmer Constant Speed and Torque Control Unit. The desired degree of polymerization was attained in about 60 to 90 minutes.

The inherent viscosity of the condensation polymer was measured in a 1:1 by weight mixture of phenol:chlorobenzene at 25° C. at a concentration of 0.25 grams/100 mL of solution using a GCA/Precision Scientific Viscometer; {η}=0.20.

EXAMPLES 3–13

Condensation polymers containing dimethyl 5-(4-sodiosulfocyclohexyloxy)-1,3-cyclohexanedicarboxylate The compound dimethyl 5-(4-sodiosulfocyclohexyloxy)-1,3-cyclohexanedicarboxylate (J) was condensation polymerized with the following functionalized compounds according to the procedure of Example 2:

HOC$_2$H$_4$OH     A

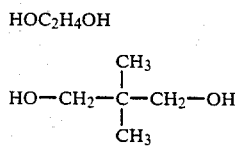     B

-continued

HO—C$_2$H$_4$OC$_2$H$_4$OH     C

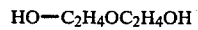     D

     E

     F

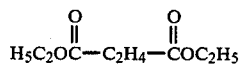     G

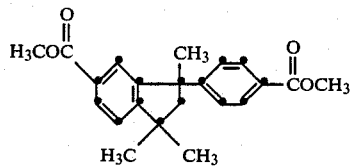

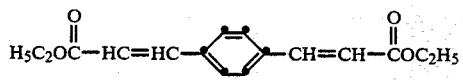     H

     I

Table II lists the compositions of the condensation polymers prepared and the inherent viscosity, glass transition temperature and solubility characteristics of each polymer.

TABLE II

| Example | A | B | C | D | E | F | G | H | I | J | (η)* | Tg, °C | Solubility |
|---|---|---|---|---|---|---|---|---|---|---|---|---|---|
| 3 | 50 | 50 | | | | | 55 | 40 | 5 | | 0.35 | 72 | DCE** |
| 4 | 50 | 50 | | | | | 75 | 20 | 5 | | 0.26 | 108 | Solvesso (an aromatic solvent derived from petroleum available from Exxon Corporation), DCE |
| 5 | 50 | 50 | | | | | 70 | 20 | 10 | | 0.19 | 103 | DCE |
| 6 | | 50 | 50 | | | | 75 | 20 | 5 | | 0.34 | 87 | Solvesso, DCE |
| 7 | | | | 100 | 85 | | | | 15 | | 0.27 | 31 | Dispersible in $H_2O$ |
| 8 | | | | 100 | 75 | | | | 25 | | 0.36 | 32 | $H_2O$ |
| 9 | | | | 100 | 70 | | | | 30 | | 0.17 | 25 | $H_2O$ |
| 10 | | | | 100 | | 5 | 55 | | 40 | | 0.21 | 54.8 | $H_2O$ |
| 11 | | | | 100 | 15 | | 55 | | 30 | | 0.26 | 36.5 | $H_2O$ |
| 12 | | | | 100 | 10 | | 65 | | 25 | | 0.31 | — | Dispersible in $H_2O$ |
| 13 | | | | 100 | | 25 | 55 | | 20 | | 0.35 | 24 | DCE |

*Viscosities run in 1:1 by weight phenol:chlorobenzene
**1,2-Dichloroethane

EXAMPLE 14

Salt tolerance of condensation polymers containing dimethyl 5-(4-sodiosulfocyclohexyloxy)-1,3-cyclohexane dicarboxylate Two 0.066 g/l aqueous solutions were prepared, the first (solution A) containing the condensation polymer of Example 3, poly[1,4-cyclohexylenebis(oxyethylene)-succinate-co-p-phenylenebis(acrylate)co-5-(4-sodiosulfocyclohexyloxy)-1,3-cyclohexane dicarboxylate] (100:10:55:35), and the second (solution B) containing the condensation polymer poly[1,4-cyclohexylenebis-(oxyethylene)succinate-co-p-phenylenebis(acrylate)-co-5-sodiosulfoisophthalate] (100:10:55:35). The turbidities of solutions A and B were monitored using a nephelometer as a 0.1 molar $CaCl_2$ solution was slowly added. A measurement of 70% relative turbidity was attained upon the addition of only 125 microliters of $CaCl_2$ solution to 1.0 ml of solution B. However, 700 microliters of the $CaCl_2$ solution was required to attain 70% relative turbidity of a sample of the same size of solution A of the invention, demonstrating the superior kinetics of coagulation and improved salt tolerance of the condensation polymer of the invention containing cycloalkylsulfonate recurring units.

EXAMPLE 15

Condensation polymer evaluation in dye imbibition photohardenable imaging materials A dye imbibition imaging element for producing a positive, continuous tone, dye image was prepared as follows.

A mordant layer was coated on a subbed poly(ethylene terephthalate) film support. The mordant layer comprised:

| Component | Coverage mg/ft² | mg/dm² |
|---|---|---|
| poly(styrene-co-N—vinylbenzyl-N,N—dimethyl-N—cyclohexylammonium chloride-co-divinylbenzene) (49:2) (mordant) | 40 | 4.3 |
| gelatin (binder) | 20 | 2.2 |
| formaldehyde (hardener) | 2 | 0.22 |
| surfactant (Surfactant 10G, which is para-isononylphenoxypolyglycidol and is a trademark and available from the Olin Corporation, U.S.A.) | 1.2 | 0.13 |

The following photohardenable layers comprising condensation polymers A,B,C,D,E and control F were coated on different samples of support having thereon the above mordant layer:

| Component | Coverage mg/ft² | mg/dm² |
|---|---|---|
| condensation polymer A,B,C,D,E or control F | 54 | 5.83 |
| 3-(7-methoxy-3-coumarinoyl)-1-methylpyridinium p-toluenesulfonate (sensitizer) | 2.7 | 0.29 |

Condensation polymers A,B,C,D,E and control F are identified below:

| | |
|---|---|
| A. | poly[1,4-cyclohexylenebis(oxyethylene) succinate-co-phenylenebis(acrylate)-co-5-(4-sodiosulfocyclohexyloxy)-1,3-cyclohexane-dicarboxylate](100:5:55:40) |
| B. | same recurring units as A in the proportions 100:10:55:35 |
| C. | same recurring units as A in the proportions 100:15:55:30 |
| D. | same recurring units as A in the proportions 100:10:65:25 |
| E. | same recurring units as A in the proportions 100:25:55:20 |
| Control F | poly[1,4-cyclohexylenebis(oxyethylene) succinate-co-phenylenebis(acrylate)-co-5-(4-sodiosulfophenoxy)isophthalate]in the proportions 100:15:55:30 |

The resulting imaging element was imagewise exposed by means of a conventional photographic step tablet for 78 seconds and by means of a mercury vapor light source (Kalvar Kalkard 200 exposing unit, which is a tradename of, and available from the Kalvar Company, U.S.A.).

The following processing steps were then carried out:
(1) 30-second rinse of the exposed element by means of running distilled or running tap water;

(2) brief swabbing by means of a cotton pad wet with distilled water or tap water;

(3) 60-second immersion in a 0.4 percent aqueous solution of the following cyan dye in a pH 10.0 buffer:

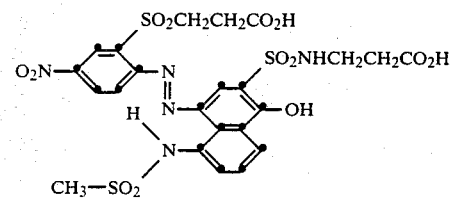

(4) 20-second rinse by means of running tap water. Each of the processing steps was carried out at room temperature (about 21° C.). A continuous tone image was produced having a gamma of 2.1 read by reflection to red light while in contact with a white paper print stock for all samples. In all samples, the image developed cleanly when distilled water was used in the spray development step (1) and the swabbing step (2).

When ordinary tap water was used in steps (1) and (2), the control condensation polymer F scummed badly, due to the exchange of the sodio salt of the 5-(4-sodiosulfophenoxy)isophthalate moiety with the mono-, di- and trivalent cationic salts in the tap water and resulted in insolubilization of the polymer. When an aqueous solution of the cationic coumarin sensitizer was quickly added to an aqueous solution of the control polymer F, a precipitate formed. This precipitate was identified as the exchange product between the sodium ion of the polymer and the pyridinium cation of the coumarin sensitizer. This formation of an aqueous insoluble polymeric coumarin, as well as the scumming of imaging elements containing the polymer, indicated that control condensation polymer F was very salt sensitive.

However, the spray development step (1) and the swabbing step (2) using ordinary tap water with condensation polymers A,B,C,D and E of the invention resulted in clean development with no scumming. Further, no polymeric coumarin precipitate formed upon the addition of the aqueous coumarin sensitizer to the aqueous condensation polymer solutions. These results demonstrated the superior salt tolerance of condensation polymers A,B,C,D and E comprising cycloalkylsulfonate recurring units over the control polymer F comprising an aromatic sulfonate recurring unit.

The invention has been described in detail with particular reference to preferred embodiments thereof, but it will be understood that variations and modifications can be effected within the spirit and scope of the invention.

What is claimed is:

1. A composition of matter having the formula:

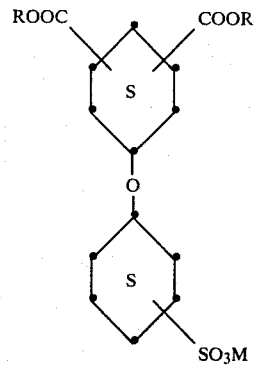

wherein:
R is alkyl containing from 1 to 10 carbon atoms; and
M is a monovalent cation selected from the group consisting of alkali metal and ammonium.

2. The composition of claim 1 wherein the —COOR groups occupy positions which are meta with respect to each other, and —SO₃M occupies a para position.

3. The composition of claim 1 wherein R is selected from the group consisting of methyl, ethyl, propyl, isopropyl, n-butyl, secondary butyl, isobutyl, t-butyl, pentyl, neopentyl, hexyl, octyl and decyl.

4. The composition of claim 3 wherein R is methyl.

5. The composition of claim 1 wherein M is a sodium ion.

6. A composition having the formula:

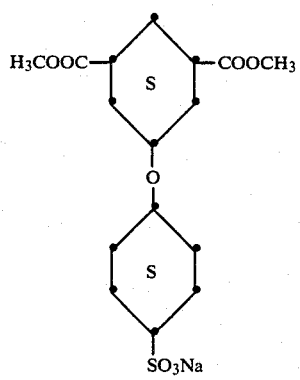

* * * * *